United States Patent
Northrop et al.

(10) Patent No.: US 11,904,108 B2
(45) Date of Patent: Feb. 20, 2024

(54) CATHETERS WITH SHAPE LOCKING MECHANISMS

(71) Applicants: STRYKER CORPORATION, Kalamazoo, MI (US); STRYKER EUROPEAN OPERATIONS LIMITED, Carrigtwohill (IE)

(72) Inventors: Clay W. Northrop, Salt Lake City, UT (US); Ted W. Layman, Park City, UT (US)

(73) Assignees: Stryker Corporation, Kalamazoo, MI (US); Stryker European Operations, Ltd., Carrigtwohill (IE)

(*) Notice: Subject to any disclaimer, the term of this patent is extended or adjusted under 35 U.S.C. 154(b) by 227 days.

(21) Appl. No.: 17/138,002

(22) Filed: Dec. 30, 2020

(65) Prior Publication Data
US 2022/0203069 A1 Jun. 30, 2022

(51) Int. Cl.
*A61M 25/00* (2006.01)

(52) U.S. Cl.
CPC ............... *A61M 25/0054* (2013.01)

(58) Field of Classification Search
CPC .. A61M 2025/0059; A61M 2025/0063; A61M 2025/09125; A61M 25/005; A61M 25/0054; A61M 2025/0004; A61M 25/0023; A61M 25/04; A61M 25/0133; A61M 25/0141; A61M 25/0144; A61M 25/0147
See application file for complete search history.

(56) References Cited

U.S. PATENT DOCUMENTS

| | | | | |
|---|---|---|---|---|
| 6,663,648 | B1* | 12/2003 | Trotta | A61M 25/104 604/103.09 |
| 10,835,112 | B2* | 11/2020 | Smith | A61B 1/0057 |
| 2003/0191451 | A1* | 10/2003 | Gilmartin | A61M 25/005 604/527 |
| 2012/0277729 | A1* | 11/2012 | Melsheimer | A61M 25/01 604/525 |

(Continued)

FOREIGN PATENT DOCUMENTS

| WO | WO 2007/022650 A1 | 3/2007 |
|---|---|---|
| WO | WO 2007/093394 A1 | 8/2007 |
| WO | WO 2018/022813 A1 | 2/2018 |

OTHER PUBLICATIONS

"Merriam-Webster Dictionary, Affix Definition & Meaning, 2023, https://www.merriam-webster.com/dictionary/affix" (Year: 2023).*

(Continued)

*Primary Examiner* — Leslie Lopez
*Assistant Examiner* — Katherine-Ph Minh Pham
(74) *Attorney, Agent, or Firm* — Vista IP Law Group, LLP

(57) ABSTRACT

A catheter includes: a tube having a distal end, a proximal end, and a tube body extending between the distal end and the proximal end, the tube having a tube wall and a first channel in the tube wall; a first elongated element located in the first channel of the tube, the first elongated element slidably moveable in the first channel relative to the tube wall; and a suction port configured to apply suction in the first channel; wherein a first part of the tube wall is configured to deform to apply a first force against the first elongated element in response to the suction in the first channel.

19 Claims, 6 Drawing Sheets

(56) References Cited

U.S. PATENT DOCUMENTS

2016/0030704 A1\* 2/2016 Nishigishi ......... A61M 25/0054
  604/103
2020/0086090 A1\* 3/2020 von Weymarn-Schärli .................
  A61M 25/0662

OTHER PUBLICATIONS

PCT International Search Report and Written Opinion for International Appln. No. PCT/US2021/065244, Applicant Stryker Corporation, dated May 17, 2022 (15 pages).

\* cited by examiner

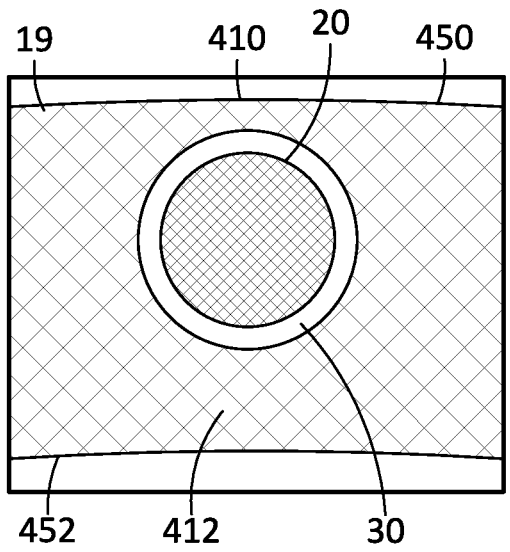
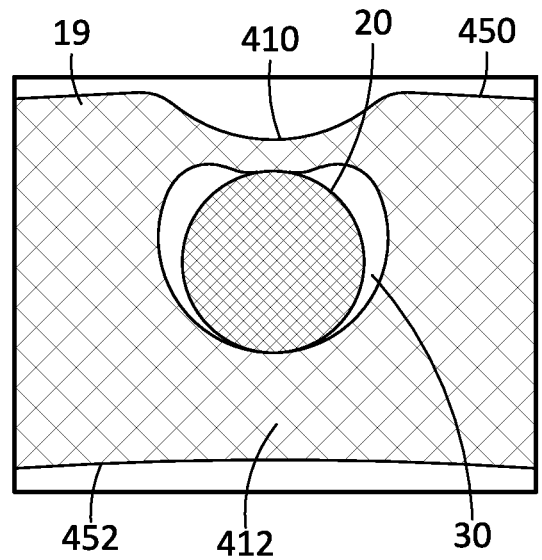
FIG. 4A
FIG. 4B
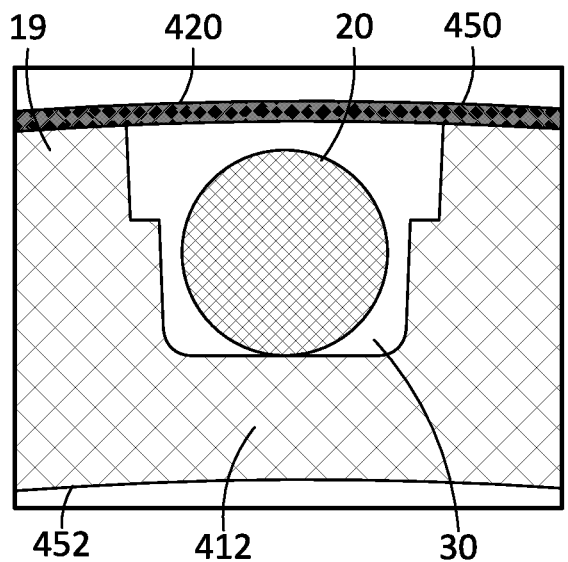
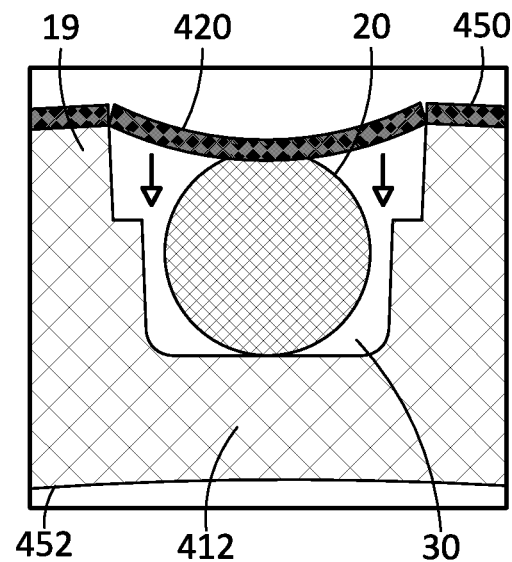
FIG. 5A
FIG. 5B

CATHETERS WITH SHAPE LOCKING MECHANISMS

FIELD

The present disclosure relates generally to minimally invasive medical devices, and more specifically to catheters.

BACKGROUND

The use of intravascular catheters for accessing and treating various types of diseases, such as vascular defects, is well-known. For example, a suitable intravascular catheter may be inserted into the vascular system of a patient. Commonly used vascular application to access a target site in a patient involves inserting a guidewire through an incision in the femoral artery near the groin, and advancing the guidewire until it reaches the target site. Then, a catheter is advanced over the guidewire until an open distal end of the catheter is disposed at the target site. Simultaneously or after placement of the distal end of the catheter at the target site, an intravascular implant is advanced through the catheter via a delivery wire.

Catheters may also be employed to deliver other substances (such as drugs, diagnostic agents, medicines, etc.) into a patient, and/or to remove substances (such as tissue samples, blood, target tissue, etc.) from within a patient.

In certain applications, such as neurovascular treatment, the catheters are required to navigate tortuous and intricate vasculature. By using an appropriately sized device having the requisite performance characteristics, the catheter may navigate to a target through the tortuous vasculature. In some cases, a catheter may have a very small cross-sectional dimension in order to reach small blood vessels. Such catheter may also be required to be very flexible in order for the catheter to navigate through tight bends in the vasculature. Existing catheter with steering control at the handle may be too stiff and/or may not be able to bend into a small curvature. Also, such existing catheter may not allow a user to selectively stiffen the catheter to lock the catheter with any bent shape in-situ.

SUMMARY

New techniques for stiffening catheters in-situ are described herein. In one or more embodiments described herein, a catheter may be freely and selectively bent into any desired shape in-situ. After a desired shape of the catheter is achieved in-situ, the catheter may be stiffened to lock the shape of the catheter.

A catheter includes: a tube having a distal end, a proximal end, and a tube body extending between the distal end and the proximal end, the tube having a tube wall and a first channel in the tube wall; a first elongated element located in the first channel of the tube, the first elongated element slidably moveable in the first channel relative to the tube wall; and a suction port configured to apply suction in the first channel; wherein a first part of the tube wall is configured to deform to apply a first force against the first elongated element in response to the suction in the first channel.

Optionally, the first part of the tube wall comprises a layer of the tube wall that is disposed radially with respect to the first elongated element.

Optionally, the layer of the tube wall is integrally formed with a remaining part of the tube wall.

Optionally, the layer of the tube wall comprises a cover that is disposed over the first channel to cover the first elongated element, wherein the cover is secured to a remaining part of the tube wall.

Optionally, the first elongated element has different cross-sectional dimensions at different respective locations along a length of the first elongated element.

Optionally, the first channel has different cross-sectional dimensions at different respective locations along a length of the first channel.

Optionally, the tube has a second channel in the tube wall, and wherein the catheter further comprises a second elongated element located in the second channel of the tube, the second elongated element slidably moveable in the second channel relative to the tube wall; and wherein a second part of the tube wall is configured to deform to apply a second force against the second elongated element.

Optionally, the suction port is configured to apply suction in both the first channel and the second channel.

Optionally, the first elongated element and the second elongated element have different respective lengths.

Optionally, the first elongated element and the second elongated element are on opposite sides of the tube.

A catheter includes: a tube having a distal end, a proximal end, and a tube body extending between the distal end and the proximal end, the tube having a tube wall, a first channel in the tube wall, and a first fluid channel in the tube wall; a first elongated element located in the first channel of the tube, the first elongated element slidably moveable in the first channel relative to the tube wall; and a fluid delivery port configured to provide fluid in the first fluid channel; wherein a first part of the tube wall is configured to deform to apply a first force against the first elongated element in response to the fluid in the first fluid channel.

Optionally, the first part of the tube wall is located between the first channel and the first fluid channel.

Optionally, the tube further comprises a second fluid channel, wherein the fluid delivery port is configured to provide fluid in the second fluid channel; and wherein a second part of the tube wall is configured to deform to apply a second force against the first elongated element in response to the fluid in the second fluid channel.

Optionally, the first channel is located between the first fluid channel and the second fluid channel.

Optionally, the first elongated element has different cross-sectional dimensions at different respective locations along a length of the first elongated element.

Optionally, the first channel has different cross-sectional dimensions at different respective locations along a length of the first channel.

Optionally, the tube has a second channel and a second fluid channel in the tube wall, and wherein the catheter further comprises a second elongated element located in the second channel of the tube, the second elongated element slidably moveable in the second channel relative to the tube wall; and wherein a second part of the tube wall is configured to deform to apply a second force against the second elongated element.

Optionally, the fluid delivery port is also configured to provide fluid in the second fluid channel to cause the second part of the tube wall to deform.

Optionally, the first elongated element and the second elongated element have different respective lengths.

Optionally, the first elongated element and the second elongated element are on opposite sides of the tube.

Other and further aspects and features of embodiments will become apparent from the ensuing detailed description in view of the accompanying figures.

BRIEF DESCRIPTION OF THE FIGURES

FIG. 4A illustrates a partial cross-section of the catheter of FIG. 1A or 1B, particularly showing an elongated member in a tube wall being in an unlocked state.

FIG. 4B illustrates a partial cross-section of the catheter of FIG. 1A or 1B, particularly showing an elongated member in a tube wall being in a locked state.

FIG. 5A illustrates a variation of the catheter of FIG. 1A or 1B, particular showing an elongated member in a tube wall being in an unlocked state.

FIG. 5B illustrates a variation of the catheter of FIG. 1A or 1B, particular showing an elongated member in a tube wall being in a locked state.

DETAILED DESCRIPTION

Figure 1A:
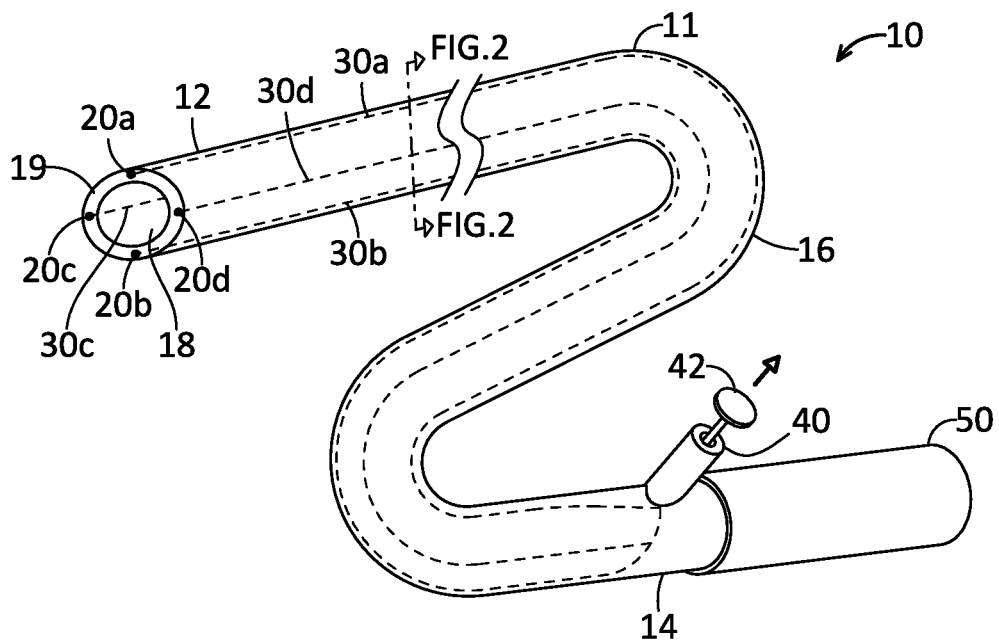
FIG. 1A illustrates a catheter in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. In some cases, the term "about" may refer to a range of values that are within +/−10% of a value. For example, a value of 2 or a value of about 2 may refer to any value that is within the range of 2+/−10% (=2+/−0.2=1.8 to 2.2).

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Figure 1B:
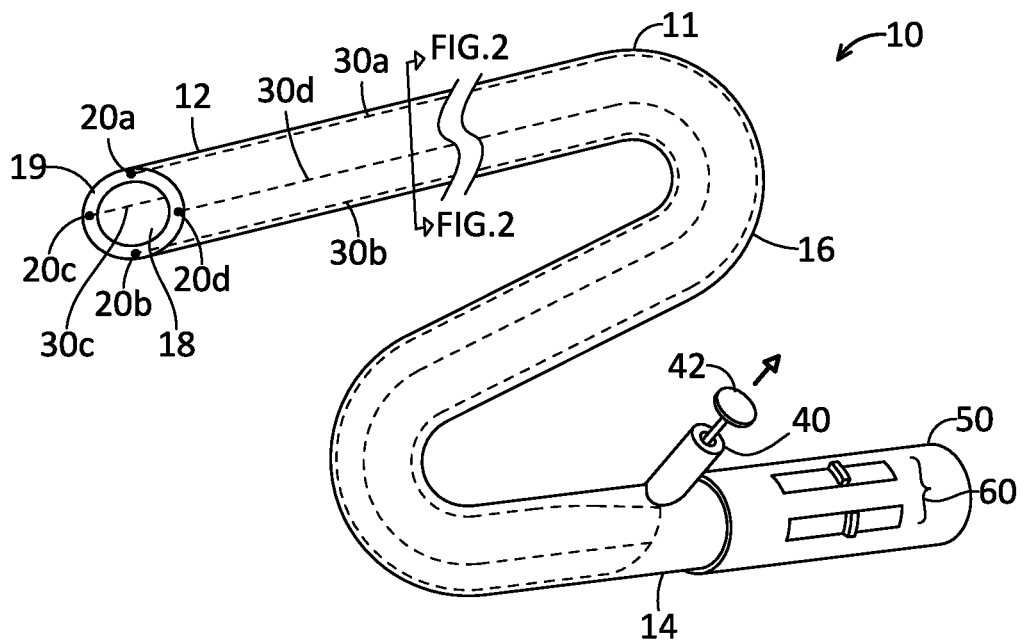
FIG. 1B illustrates a variation of the catheter of FIG. 1A.
Figure 2:
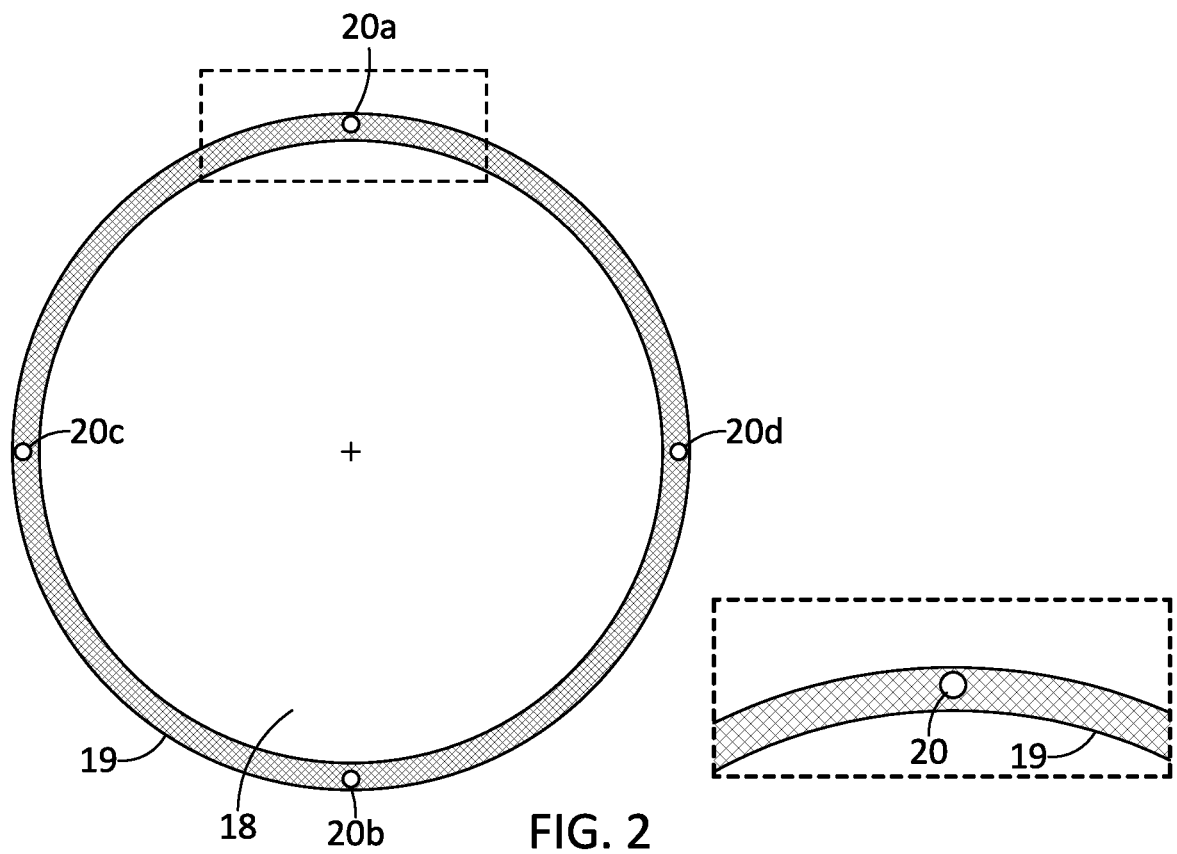
FIG. 2 illustrates a cross-section of the catheter of FIG. 1A or 1B.

FIGS. 1-2 illustrate a catheter 10 in accordance with some embodiments. The catheter 10 includes a tube 11 having a distal end 12, a proximal end 14, and a tube body 16 extending between the distal end 12 and the proximal end 14. The tube 11 has a tube wall 19, and channels 30a-30d in the tube wall 19 configured to accommodate respective elongated elements 20a-20d. The elongated elements 20a-20d have respective distal ends that are fixed in position with respect to the tube wall 19. For example, the distal ends of the elongated elements 20a-20d may be secured directly or indirectly to the tube wall 19 via an adhesive, an anchor, a mechanical connector, etc. The elongated elements 20a-20d (i.e., the parts of the elongated elements 20a-20d that are not secured relative to the tube wall 19) are slidably moveable in the respective channels 30a-30d relative to the tube wall 19 in association with a bending of the catheter 10. The catheter 10 also includes a suction port 40 configured to apply suction in the channels 30a-30d in response to movement of control 42.

The catheter 10 further includes a handle 50. In the illustrated embodiments, the catheter 10 does not include any steering control, and the elongated elements 20a-20d are free to slide relative to the respective channels 30a-30d when the catheter 10 assumes any bent shape. For example, as the catheter 10 is being advanced in a vessel, the catheter 10 may itself assume a bent shape due to a curvature of the vessel. Alternatively, the catheter 10 may also itself assume a bent shape as it is being advanced over a guidewire inside a patient. In some embodiments, the elongated elements 20a-20d have respective proximal ends that are unfixed to the tube body 16, and are free to translate axially relative to the tube wall 19 during bending of the catheter 10. In some embodiments, the entire length of the elongated element 20 may be accommodated in the corresponding channel 30. In other embodiments, the proximal end of the elongated element 20 may extend out of the proximal end of the channel 30. In such cases, the proximal end of the channel 30 may have a seal with an opening for allowing the elongated element 20 to extend therethrough. The seal provides a fluid seal between the elongated element 20 and the channel 30 while allowing the elongated element 20 to translate relative to the channel 30.

In other embodiments, the catheter 10 may optionally further include one or more controls 60 configured to apply tension to one or more of the elongated elements 20a-20d to thereby bend the tube body 16 in one or more desired directions (FIG. 1B).

Figure 3:
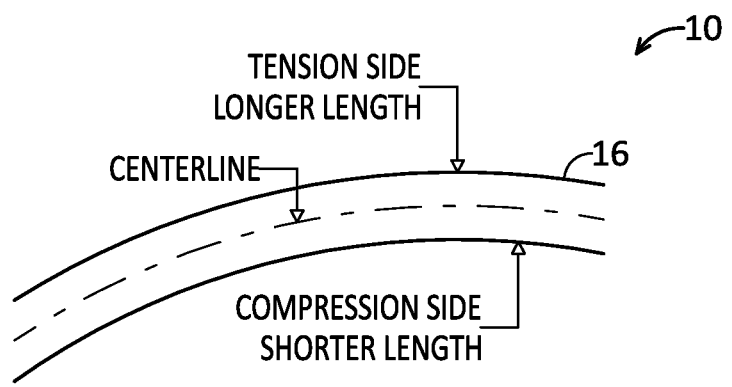
FIG. 3 illustrates a bending of a catheter.

FIG. 3 illustrates a bending of the tube body 16 of the catheter 10. As shown in the figure, when the tube body 16 is bent, one side of the tube body 16 is in tension, and an opposite side of the tube body 16 is in compression. The side of the tube body 16 that is in tension is longer than the opposite side of the tube body 16 that is in compression. Accordingly, when the tube body 16 is bent, a part of the elongated element 20 on the tension side of the tube body 16 will move relative to a part of the tube body 16, and a part of another elongated element 20 on the compression side of the tube body 16 will also move relative to a part of the tube body 16. In some embodiments, the channels 30 and the elongated elements 20 are sized so that there is sufficient clearance between the elements 20 and the surfaces of the channels 30 for allowing the elongated elements 20 to freely move within the respective channels 30.

During use, the catheter 10 is inserted into a blood vessel in a patient, and is advanced distally. The catheter 10 may freely bend inside the blood vessel by following the curvature of the blood vessel. In some cases, a guidewire may be delivered into the blood vessel first, and then the catheter 10 may be placed over the guidewire, and may use the guidewire to navigate through a vasculature. As the catheter 10 is being advanced over the guidewire, the catheter 10 is also free to bend to assume any shape following the profile of the guidewire. At any moment during the navigation of the catheter 10, a user of the catheter 10 may want to lock a bent shape of the catheter 10. In such cases, the user may operate the control 42 (e.g., by pulling the control 42) to apply suction in the channels 30a-30d via the suction port 40. The suction in the channels 30a-30d causes respective parts of the tube wall 19 to deform towards respective elongated members 20a-20d. As a result, the deformed parts of the tube wall 19 apply respective forces against the respective elongated elements 20a-20d in response to the suction in the respective channels 30a-30d. The forces lock the elongated elements 20a-20d against the tube body 16, thereby preventing the elongated elements 20a-20d to slide relative to the tube body 16. This in turn will cause a shape of the catheter 10 to be locked. This effect is realized because the elongated element(s) 20 on the inside of any curve in the catheter 10 would be in tension if any forces were applied that would tend to straighten out the curve of the catheter 20—e.g., via advancement of a relatively stiff elongated device (e.g., treatment device or diagnostic device) through the catheter. In order for the curve of the catheter 20 to straighten out, the aforementioned elongated member 20 would have to stretch longitudinally. Such an elongated member 20 comprising isotropic material will have a longitudinal (tensile) stiffness that is disproportionately large relative to its lateral (bending) stiffness, and therefore its contribution to the catheter stiffness is much greater in its locked state than it is in its unlocked state.

As shown in FIG. 4A, the elongated member 20 in the tube wall 19 may be in an unlocked state when no suction is applied in the channel 30. When in the unlocked state, the elongated member 20 in the tube wall 19 is free to slide in the channel 30 relative to the tube wall 19. As shown in FIG. 4B, the elongated member 20 in the tube wall 19 is in a locked state when suction is applied in the channel 30, causing a part 410 of the tube wall 19 to deform towards the elongated member 20 to compress against the elongated member 20. When in the locked state, frictional forces between the elongated member 20 and surrounding surfaces defining the channel 30 (including the surface of the part 410) prevent the elongated member 20 from moving relative to the tube wall 19.

As shown in FIG. 4A, the elongated member 20 and the channel 30 are located closer to the outer surface 450 of the tube wall 19 than to the inner surface 452 of the tube wall 19. This results in the part 410 with a thickness that is thinner than another part 412 of the tube wall 19 on the opposite side of the channel 30, so that the part 410 (instead of the part 412) will deform in response to the suction in the channel 30. In other embodiments, the elongated member 20 and the channel 30 may be located closer to the inner surface 452 of the tube wall 19 than to the outer surface 450. This results in the part 412 with a thickness that is thinner than the part 410 of the tube wall 19 on the opposite side of the channel 30, so that the part 412 (instead of the part 410) will deform in response to the suction in the channel 30.

In the above embodiments, the channel 30 has a cross-sectional shape (when no suction is applied) that is circular. In other embodiments, the cross-section of the channel 30 may have any of other shapes, such as an elliptical shape, a square shape, a rectangular shape, a customized shape, etc.

Also, in some embodiments, the channel 30 may have the same size and cross-sectional dimension along a majority of its length (e.g., along its entire length). In other embodiments, different parts (e.g., segments) of the channel 30 may have different shapes and/or cross-sectional dimensions. In further embodiments, if the device has multiple channels 30, the channels 30 may have the same shapes and/or cross-sectional dimensions. In other embodiments, the channels 30 may have different respective shapes and/or cross-sectional dimensions.

In the above embodiments, the part 410 of the tube wall 19 is a layer of the tube wall 19 that is integrally formed with a remaining part of the tube wall 19. The layer of the tube wall 19 is disposed radially with respect to the elongated element 20.

In other embodiments, the part 410 of the tube wall 19 may comprise a cover 420 that is disposed over the channel 30 to cover the elongated element 20 (FIGS. 5A-5B). In such cases, the cover 420 may be secured to a remaining part of the tube wall 19. The cover 420 may be implemented using a thin and flexible layer of polymer in some embodiments. In other embodiments, the cover 420 may be implemented using other structures made from other materials. As shown in FIG. 5A, the elongated member 20 in the tube wall 19 may be in an unlocked state when no suction is applied in the channel 30. When in the unlocked state, the elongated member 20 in the tube wall 19 is free to slide in the channel 30 relative to the tube wall 19. As shown in FIG. 5B, the elongated member 20 in the tube wall 19 is in a locked state when suction is applied in the channel 30, causing the cover 420 to deform towards the elongated member 20 to compress against the elongated member 20. When in the locked state, frictional forces between the elongated member 20 and surrounding surfaces defining the channel 30 (including the surface of the cover 420) prevent the elongated member 20 from moving relative to the tube wall 19.

In the above embodiments of FIGS. 5A-5B, the channel 30 has a cross-sectional shape (when no suction is applied) that is circular. In other embodiments, the cross-section of the channel 30 may have any of other shapes, such as an elliptical shape, a square shape, a rectangular shape, a customized shape, etc.

Also, with reference to FIGS. 5A-5B, in some embodiments, the channel 30 may have the same size and cross-sectional dimension along a majority of its length (e.g., along its entire length). In other embodiments, different parts (e.g., segments) of the channel 30 may have different shapes and/or cross-sectional dimensions. In further embodiments, if the device has multiple channels 30, the channels 30 may have the same shapes and/or cross-sectional dimensions. In other embodiments, the channels 30 may have different respective shapes and/or cross-sectional dimensions.

Figure 6:
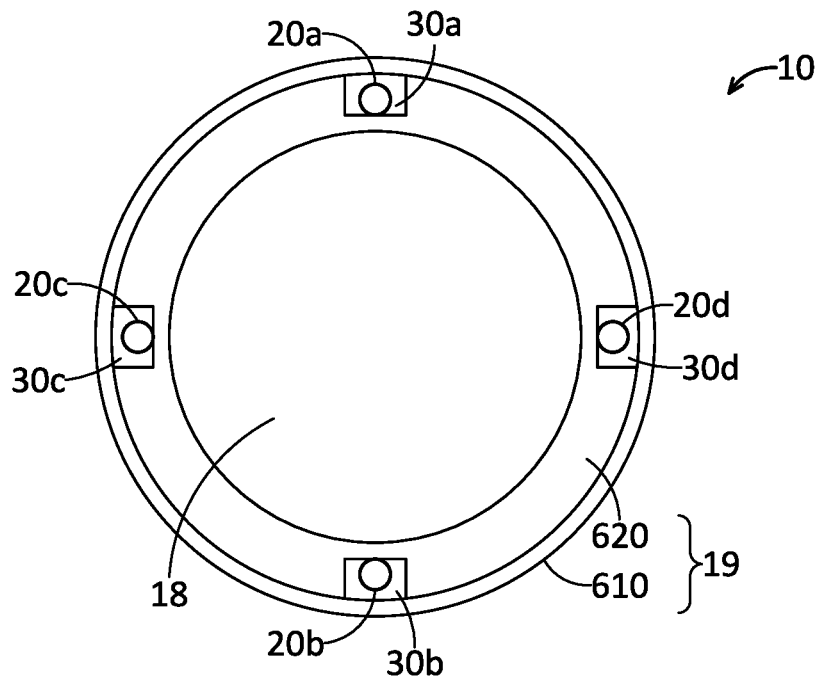
FIG. 6 illustrates an implementation of the catheter of FIGS. 5A-5B.

FIG. 6 illustrates an implementation of the catheter of FIGS. 5A-5B. As shown in the figure, the cover 420 may be implemented using a tubular layer 610 (e.g., a sheath) disposed over a remaining part 620 of the tube wall 19. In such cases, the tubular layer 610 provides multiple covers 420 covering the respective elongated members 20 in the respective channels 30. The tubular layer 610 may be secured to the remaining part 620 of the tube wall 19 via an adhesive (such as glue), via friction, or may be formed circumferentially around the part 620 of the tube wall 19. In further embodiments, the tubular layer 610 may be laminated onto the part 620 of the tube wall 19.

In other embodiments, instead of the tubular layer 610, the catheter 10 may include multiple individual covers 420 secured to the part 620 of the tube wall 19. The securing may be achieved using an adhesive in some embodiments. In other embodiments, the covers 420 may be formed on the part 620 of the tube wall 19. In further embodiments, the covers 420 may be laminated onto the part 620 of the tube wall 19.

In the above embodiments, the elongated member 20 is illustrated as having a circular cross-section. In other embodiments, the elongated member 20 may have a non-circular cross-section. For example, in other embodiments, the elongated member 20 may have an elliptical cross-section, a square cross-section, a rectangular cross-section, or any of other cross-sectional shapes.

Figures 7A, 7B:
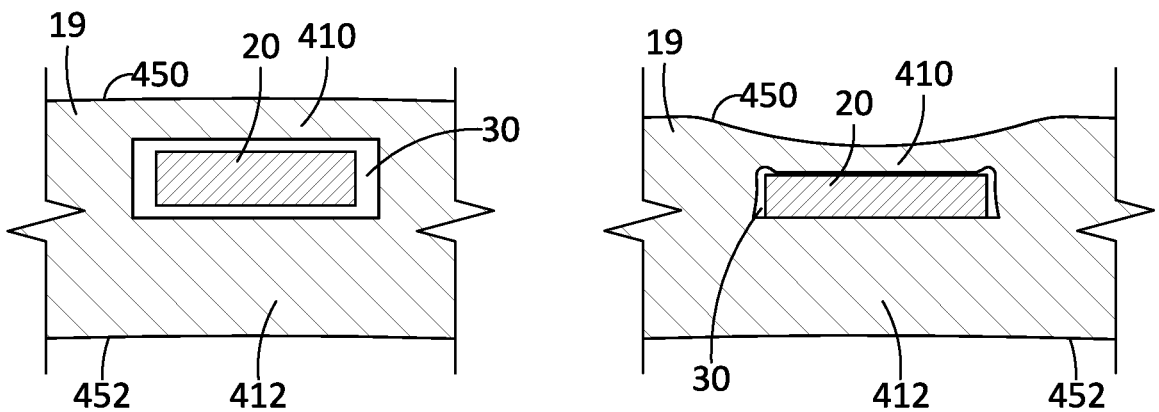
FIGS. 7A-7B illustrate a variation of the catheter of FIG. 1A or 1B, particular showing an elongated member with a non-circular cross-sectional shape.

In some embodiments, if the cross-section of the elongated member 20 is wider in one direction than in another direction, it may be advantageous to orient the elongated member 20 so that the wider side of the cross-section is facing the part 410 of the tube wall 19. For example, as shown in FIG. 7A, the elongated member 20 may have a rectangular cross-section. In such cases, the long side of the cross-section of the elongated member 20 is oriented to face the part 410 of the tube wall 19. This is advantageous because when the part 410 deforms to press against the elongated member 20 (FIG. 7B), there will be more contact area between the surface of the part 410 and the elongated member 20. This results in more frictional force between the part 410 and the elongated member 20, forming a more secured lock that locks the elongated member 20 in place relative to the tube wall 19. Additionally, the elongated member 20 in its unlocked state will contribute less bending stiffness to the structure in this orientation.

In one or more embodiments described herein, the elongated element 20 may have different cross-sectional dimensions at different respective locations along a length of the elongated element 20. Such configuration may allow certain segment(s) of the elongated member 20 at different longitudinal positions along the length of the elongated member 20 to be more easily pressed against by the part 410 of the tube wall 19.

Also, in one or more embodiments, the channel 30 may have different cross-sectional dimensions at different respective locations along a length of the channel 30. Such configuration may allow certain segment(s) of the elongated member 20 at different longitudinal positions along the length of the elongated member 20 to be more easily pressed against by the part 410 of the tube wall 19.

In addition, in one or more embodiments, the part 410 of the tube wall 19 may have different thicknesses at different respective locations along a length of the tube 11. Such configuration may allow certain segment(s) of the part 410 at different longitudinal positions along the length of the tube 11 to be more easily deformed (due to suction within the channel 30). As a result, different segment(s) of the elongated member 20 may be pressed against by the part 410 with different forces along the length of the elongated member 20.

Additionally or alternatively, the part of the tube wall 19 that is configured to deform in response to suction may have different durometer or stiffness at different respective locations along the length of the tube 11. Such configuration may also allow certain segment(s) of the part (e.g., part 410) of the wall at different longitudinal positions along the length of the tube 11 to be more easily deformed (due to suction within the channel 30), thereby varying the locking force at different locations along the length of the tube 11. As a result, different segment(s) of the elongated member 20 may be pressed against by the part 410 with different forces along the length of the elongated member 20.

In the above embodiments, the catheter 10 has one suction port 40 configured to apply suction in multiple channels 30. In other embodiments, the catheter 10 may have multiple suction ports 40 and multiple corresponding controls 42 for applying suction in the respective channels 30. Such configuration allows a user to selectively apply suction in one or more of the channels 30 by manipulating one or more of the controls 42.

Figure 8A:
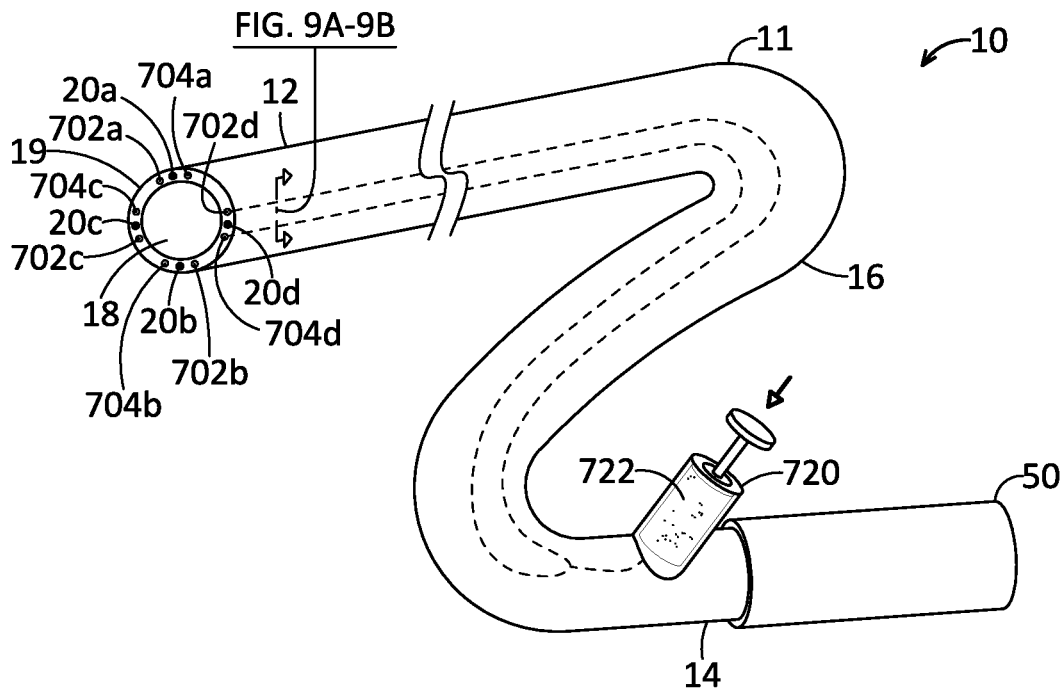
FIG. 8A illustrates another catheter in according to some embodiments.
Figure 8B:
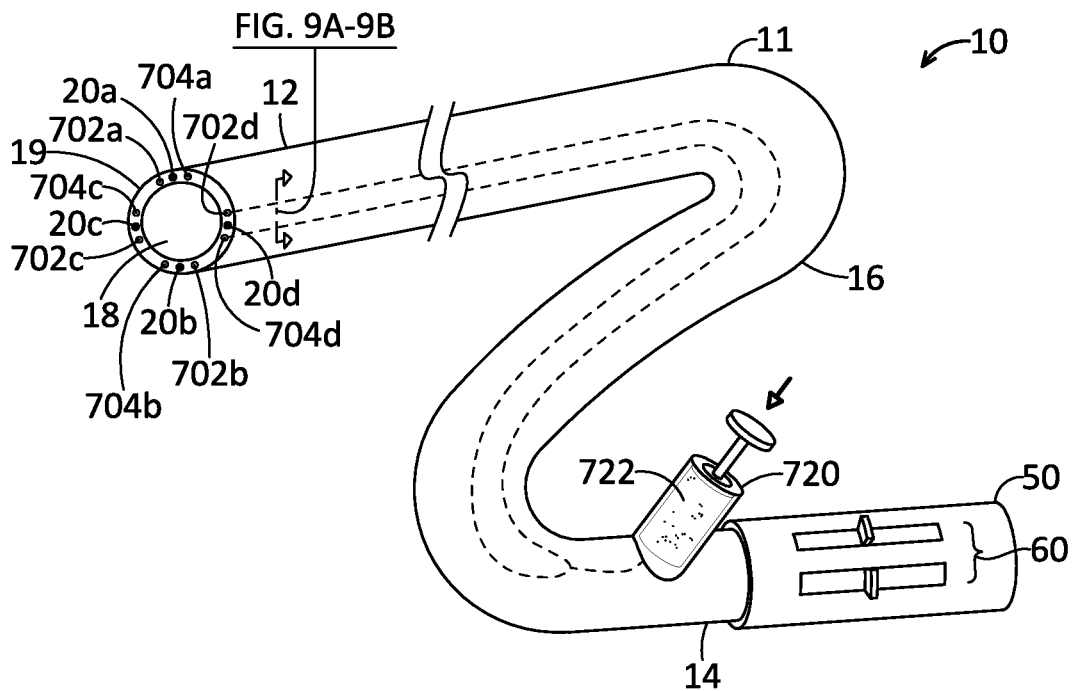
FIG. 8B illustrates a variation of the catheter of FIG. 8A.

FIG. 8A illustrates another catheter 10 in according to some embodiments. The catheter 10 includes a tube 11 having a distal end 12, a proximal end 14, and a tube body 16 extending between the distal end 12 and the proximal end 14. The tube 11 has a tube wall 19, and channels 30a-30d in the tube wall 19 configured to accommodate respective elongated elements 20a-20d. The elongated elements 20a-20d are slidably moveable in the respective channels 30a-30d relative to the tube wall 19. The catheter 10 further includes a handle 50. In the illustrated embodiments, the catheter 10 does not include any steering control, and the elongated elements 20a-20d are free to slide relative to the respective channels 30a-30d when the catheter 10 assumes any bent shape. For example, as the catheter 10 is being advanced in a vessel, the catheter 10 may itself assume a bent shape due to a curvature of the vessel. Alternatively, the catheter 10 may also itself assume a bent shape as it is being advanced over a guidewire inside a patient. In other embodiments, the catheter 10 may optionally further include one or more controls 60 configured to apply tension to one or more of the elongated elements 20a-20d to thereby bend the tube body 16 in one or more desired directions (FIG. 8B).

The catheter 10 of FIG. 8A is the same as that of FIG. 1A, except that it further includes fluid channels 702, 704 on opposite sides of each elongated element 20, and a fluid delivery unit 720 configured to deliver fluid 722 into the fluid channels 702, 704.

During use, the catheter 10 of FIG. 8A is inserted into a blood vessel in a patient, and is advanced distally. The catheter 10 may freely bend inside the blood vessel by following the curvature of the blood vessel. In some cases, a guidewire may be delivered into the blood vessel first, and then the catheter 10 may be placed over the guidewire, and may use the guidewire to navigate through a vasculature. As the catheter 10 is being advanced over the guidewire, the catheter 10 is also free to bend to assume any shape following the profile of the guidewire. At any moment during the navigation of the catheter 10, a user of the catheter 10 may want to lock a bent shape of the catheter 10. In such cases, the user may operate the fluid delivery unit 720 to deliver the fluid 722 into the fluid channels 702a-702d, 704a-704d via a fluid port. The fluid pressure in the fluid channels 702a-702d, 704a-704d causes respective parts of the tube wall 19 to deform towards respective elongated members 20a-20d. As a result, the deformed parts of the tube wall 19 apply respective forces against the respective elongated elements 20a-20d in response to the fluid pressure in the fluid channels 702a-702d, 704a-704d. The forces lock the elongated elements 20a-20d against the tube body 16, thereby preventing the elongated elements 20a-20d to slide relative to the tube body 16. This in turn will cause a shape of the catheter 10 to be locked.

Figure 9A:
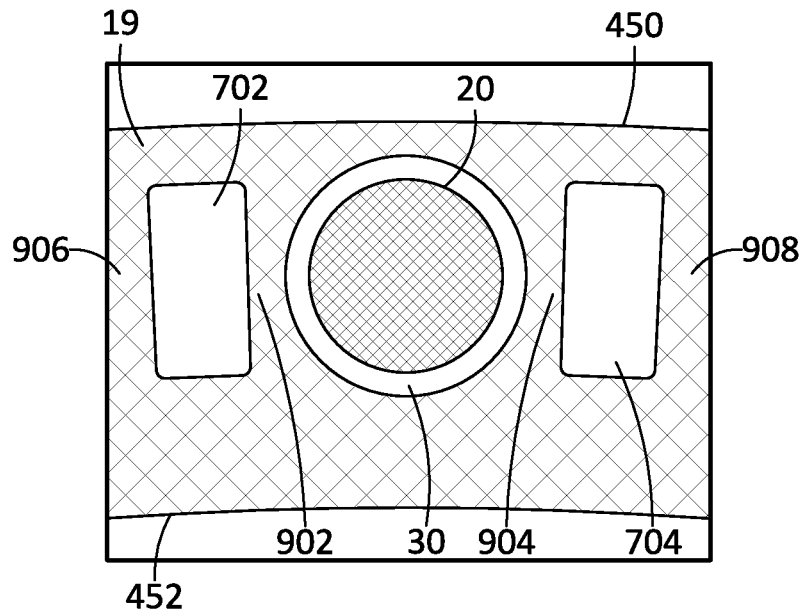
FIG. 9A illustrates a partial cross-section of the catheter of FIG. 8A or 8B, particularly showing an elongated member in a tube wall being in an unlocked state.
Figure 9B:
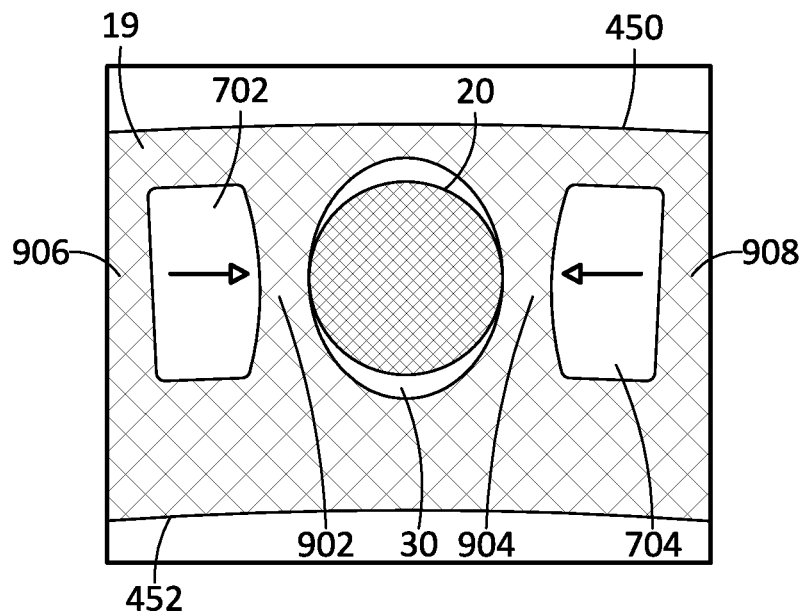
FIG. 9B illustrates a partial cross-section of the catheter of FIG. 8A or 8B, particularly showing an elongated member in a tube wall being in a locked state.

As shown in FIG. 9A, the elongated member 20 in the tube wall 19 may be in an unlocked state when no fluid pressure is applied in the fluid channels 702, 704. When in the unlocked state, the elongated member 20 in the tube wall 19 is free to slide in the channel 30 relative to the tube wall 19. As shown in FIG. 9B, the elongated member 20 in the tube wall 19 is in a locked state when fluid pressure is applied in the channels 702, 704, causing parts 902, 904 of the tube wall 19 on opposite sides of the channel 30 to deform towards the elongated member 20 to compress against the elongated member 20. When in the locked state, frictional forces between the elongated member 20 and surrounding surfaces defining the channel 30 (including the surfaces of the parts 902, 904) prevent the elongated member 20 from moving relative to the tube wall 19.

As shown in FIG. 9A, the fluid channel 702 is between parts 902, 906 of the tube wall 19. The part 902 is thinner than the part 906 due to the presence of the channel 30 next to the part 902. This results in the part 902 with a thickness that is thinner than another part 906 of the tube wall 19 on the opposite side of the fluid channel 702, so that the part 902 will deform more than the part 906 in response to the fluid pressure in the fluid channel 702. Similarly, the fluid channel 704 is between parts 904, 908 of the tube wall 19. The part 904 is thinner than the part 908 due to the presence of the channel 30 next to the part 904. This results in the part 904 with a thickness that is thinner than another part 908 of the tube wall 19 on the opposite side of the fluid channel 704, so that the part 904 will deform more than the part 908 in response to the fluid pressure in the fluid channel 704. The deformed parts 902, 904 both move towards the channel 30, changing the shape of the channel 30, and causing the surfaces of the channel 30 to compress against the elongated element 20.

In other embodiments, instead of having two fluid channels 702, 704 on opposite sides of the channel 30 accommodating the elongated element 20, the catheter 10 may have more than two fluid channels (e.g., three fluid channels, four fluid channels, etc.) disposed circumferentially around the channel 30. Also, in further embodiments, the catheter 10 may have only one fluid channel next to the channel 30 for applying fluid pressure to press a part of the tube wall 19 towards the channel 30.

In the embodiments of FIGS. 8A and 8B, the elongated members 20 are illustrated as having a circular cross-section. In other embodiments, the elongated members 20 may have a non-circular cross-section. For example, in other embodiments, an elongated member 20 may have an elliptical cross-section, a square cross-section, a rectangular cross-section, or any of other cross-sectional shapes.

In the embodiments of FIGS. 8A and 8B, the elongated element 20 may have different cross-sectional dimensions at different respective locations along a length of the elongated element 20. Such configuration may allow certain segment(s) of the elongated member 20 at different longitudinal positions along the length of the elongated member 20 to be more easily pressed against by the part 902 and/or the part 904 of the tube wall 19.

Also, in the embodiments of FIGS. 8A and 8B, the channel 30 may have different cross-sectional dimensions at different respective locations along a length of the channel 30. Such configuration may allow certain segment(s) of the elongated member 20 at different longitudinal positions along the length of the elongated member 20 to be more easily pressed against by the part 902 and/or the part 904 of the tube wall 19.

In addition, in the embodiments of FIGS. 8A and 8B, the part 902 and/or the part 904 of the tube wall 19 may have different thicknesses at different respective locations along a length of the tube 11. Such configuration may allow certain segment(s) of the part 902 and/or the part 904 at different longitudinal positions along the length of the tube 11 to be more easily deformed (due to suction within the channel 30). As a result, different segment(s) of the elongated member 20 may be pressed against by the part 902 and/or the part 904 with different forces along the length of the elongated member 20.

Embodiments of the catheter 10 described herein are advantageous because they provide simple locking mechanisms to lock elongated element(s) against the tube 11 of the catheter 10. Also, in some embodiments, the catheter 10 does not need the steering control 60 to maintain a bent shape because the locking mechanisms described herein can take over this function. In the embodiments in which the catheter 10 does not include any steering control, the catheter 10 can bend freely (e.g., by following a curvilinear path of a vasculature, and/or by being guided by a guidewire), and the locking mechanisms described herein can be utilized to lock the catheter 10 in any desired bent shape while the catheter 10 is inside the patient. In addition, in the embodiments in which the catheter 10 does not include any steering control, the catheter 10 can be made more flexible in its unlocked state (compared to catheter with steering control). This may allow for a thinner wall design for the catheter 10 than would otherwise be possible, and may allow better tracking of the catheter 10. Furthermore, because the cross-sectional size of the channel 30 is small compared to the cross-sectional size of the tube lumen 18, the catheter 10 with the features described herein is less likely to straighten, change length, or move when locked (compared to another design in which an annular space between a delivery lumen and a catheter exterior wall operates as a pressure chamber to stiffen the catheter).

In the above embodiments of FIGS. 1-9, the elongated member 20 may be made from different materials in different embodiments. By means of non-limiting examples, the elongated member 20 may be made from metal, alloy, polymer, nylon, etc. The elongated member 20 may be implemented using a wire, a ribbon, a string, a fishing wire, a suture, etc.

In some embodiments, the elongated member 20 may have a cross-sectional dimension that is less than 0.01 inch, less than 0.008 inch, less than 0.006 inch, less than 0.004 inch, or less than 0.003 inch (e.g., 0.002 inch). In other embodiments, the elongated member 20 may have a cross-sectional dimension that is larger than 0.01 inch. Also, in further embodiments, the elongated member 20 may have a cross-sectional dimension that is less than 0.002 inch.

In some embodiments, the tube wall 19 may have a thickness that is less than 0.5 inch, less than 0.4 inch, less than 0.3 inch, less than 0.2 inch (e.g., 0.1 inch), less than 0.1 inch, less than 0.05 inch, less than 0.03 inch, less than 0.02 inch, less than 0.01 inch (e.g., anywhere from 0.002 inch to 0.01 inch). In other embodiments, the tube wall 19 may have a thickness that is more than 0.5 inch, or less than 0.002 inch.

In some embodiments, the elongated elements 20 may all have the same length. In other embodiments, one elongated element 20 (e.g., first elongated element) and another elongated element 20 (e.g., second elongated element) may have different respective lengths.

Also, in some embodiments, the elongated elements 20 may have respective distal ends that terminate at a same longitudinal position along a longitudinal axis of the tube 11. In other embodiments, one elongated element 20 (e.g., first elongated element) may have a first distal end, and another elongated element 20 (e.g., second elongated element) may have a second distal end, wherein the first and second distal ends of the respective elongated elements 20 may terminate at different longitudinal positions along a longitudinal axis of the tube 11.

In the embodiments of FIGS. 1-9, the catheter 10 has four elongated elements 20*a*-20*d* (i.e., first elongated element 20*a*, second elongated element 20*b*, third elongated element 20*c*, fourth elongated element 20*d*) slidably disposed in four respective channels 30*a*-30*d* (i.e., first channel 30*a*, second channel 30*b*, third channel 30*c*, fourth channel 30*d*).

In other embodiments, the catheter 10 may have fewer than four elongated elements 20 and fewer than four channels 30. For example, in other embodiments, the catheter 10 may have three elongated elements 20 in three respective channels 30, may have two elongated elements 20 in two respective channels 30, or may have only one elongated element 20 in one channel 30.

In some embodiments, if the catheter 10 has two elongated element 20 (e.g., first and second elongated elements), the elongated elements 20 may be disposed on opposite sides of the tube 11. In other embodiments, the two elongated elements 20 may be disposed at 90 degrees (or at other angles) with respect to each other.

In further embodiments, the catheter 10 may have more than four elongated elements 20 in more than four respective channels 30.

In the above embodiments of FIGS. 1-9, the channels 30 and the fluid channels 702, 704 are illustrated as being parallel to the longitudinal axis of the catheter 10. In other embodiments, the channel(s) 30 may form an acute angle with respect to the longitudinal axis of the catheter 10. Also, in other embodiments, if the catheter 10 includes fluid channel 702 and/or fluid channel 704, the fluid channel 702 and/or fluid channel 704 may form an acute angle with respect to the longitudinal axis of the catheter 10. In one implementation, the channel(s) 30, the fluid channel(s) 702, the fluid channel(s) 704, or any combination of the foregoing, may form a helical or other curvilinear shapes in the tube wall 19 of the catheter 10. Also, in some embodiments, the angle between the channel 702 and/or channel 704 with respect to the longitudinal axis may change over the length of the catheter 10. For example, the angle may be zero at one or more longitudinal locations such that the channel 702 and/or channel 704 is parallel to the longitudinal axis of the catheter 10, and may be larger than zero to form an acute angle in one or more other longitudinal locations. In further embodiments, the channel 702 and/or channel 704 may extend from one side of the catheter 10 to another side of the catheter 10 (e.g. to an opposite side to thereby form an angle of 180 degrees, or to another side to form an angle that is less than 180 degrees).

Also, in some embodiments, if the catheter 10 has multiple elongated elements 20, the elongated elements 20 may have the same size (e.g., cross-sectional dimension). In other embodiments, the elongated elements 20 may have different respective sizes for providing different degrees of stiffness in different bending directions. In one or more embodiments, the elongated elements 20 may have different respective shapes and/or sizes. Furthermore, in one or more embodiments, an elongated element 20 may vary in cross-sectional size and/or shape over its length.

In some embodiments, a spacing gap between an elongated element 20 and a surface of the channel 30 may be different from a spacing gap between another elongated element 20 and a surface of another channel 30. For examples, a shape and/or size of the cross-section of the elongated element 20, a shape and/or size of the channel 30, a thickness of the part 410/902/904, or any combination of the foregoing, may be selected to achieve a certain desired spacing gap. Such configuration allows progressive stiffening of the catheter 10 by having a lumen of the channel 30 collapse at a lower level of vacuum or pressure than another lumen of the other channel 30. As a result, a degree of stiffness of the catheter 10 may be adjusted by an amount of vacuum or pressure applied. More vacuum or pressure results in more elongated elements 20 being locked, thereby providing more stiffness for the catheter 10.

In addition, in one or more embodiments, an elongated element 20 may be locked along its entire length, or along a majority of the entire length, by being compressed by part(s) of the tube wall 19. In other embodiments, the elongated element 20 may have different segments configured to provide individual (e.g., intermittent) locking areas or zones. This allows stiffness at different parts of the catheter 10 to be modulated. In one implementation, the individual locking areas/zones may be achieved by providing different clearances around the elongated element 20 at different locations along the length of the elongated element 20, so that parts of the elongated element 20 are not locked when other parts of the elongated element 20 are locked. Additionally or alternatively, the individual locking areas/zones may be achieved by intermittently reinforcing the different areas of the locking part (e.g., the part 410/902/904) of the tube wall 19 of the catheter 10, so that the reinforced areas will not deflect sufficiently to lock the corresponding parts of the elongated element 20, while the non-reinforced areas will deflect sufficiently to lock the corresponding parts of the elongated element 20.

Furthermore, in one or more embodiments described herein, a proximal portion of the catheter 10 may have more channel(s) 30 than its distal portion. This allows the catheter 10 to have more support when it is in the locked state. In other embodiments, the channels 30 may extend through the length of the catheter 10, but one or more of the elongated elements 20 may terminate nearer to the proximal end of the catheter 10 than other elongated element(s) 20.

In one or more embodiments described herein, the catheter 10 may optionally further include an additional tubular layer disposed around the tube 11. In such cases, the part 410 of the tube wall 19 is not attached to the additional tubular layer, thereby allowing the part 410 of the tube wall 19 to deform radially inward away from the additional tubular layer. In some cases, the additional tubular layer may be considered to be a part of the tube 11.

In other embodiments, instead of forming the channel(s) 30 in the tube wall 19, the channel(s) 30 may be implemented in a layer that is disposed outside and around the tube wall 19. For example, a tubular layer with channel(s) 30 may be disposed around the tube wall 19. In some cases, the tubular layer with the channel 30 may be considered as a part of the tube wall 19. In such cases, the outer tubular layer with the channel(s) 30, and the inner tubular layer, collectively form the tube 11 with the tube wall 19.

Furthermore, in one or more embodiments described herein, to prevent or at least reduce a degree of tackiness between the elongated element(s) 20 and the channel(s) 30, lubricating fluid may optionally be provided in the channel(s) 30. The lubricating fluid may be saline or any other fluid.

Although particular embodiments have been shown and described, it will be understood that it is not intended to limit the claimed inventions to the preferred embodiments, and it will be obvious to those skilled in the art that various changes and modifications (e.g., the dimensions and/or shapes of various parts) may be made without department from the scope of the claimed inventions. The specification and drawings are, accordingly, to be regarded in an illustrative rather than restrictive sense. The claimed inventions are intended to cover alternatives, modifications, and equivalents.

What is claimed is:

1. A catheter comprising: a tube having a distal end, a proximal end, and a tube body extending between the distal end and the proximal end, the tube body having a tube wall and a first channel in the tube wall; a first elongated element located in the first channel of the tube, the first elongated element slidably moveable in the first channel relative to the tube wall; and a suction port configured to apply suction in the first channel; wherein a first part of the tube wall is configured to deform to apply a first force against the first elongated element in response to the suction in the first channel; wherein the first elongated element has a first portion that is fixed in position relative to the tube wall while a second portion of the first elongated element that is not fixed to the tube wall is slidable within the first channel; wherein a segment of the first elongated element has a center that is closer to an outer side of the tube body with a first radius of curvature than to an inner surface of the tube body with a second radius of curvature that is less than the first radius of curvature, thereby allowing the outer side of the tube body to move radially more than the inner surface of the tube body when the suction is applied in the first channel, the inner surface being radially inward with respect to the first channel and defining a central tube lumen of the tube.

2. The catheter of claim 1, wherein the first part of the tube wall comprises a layer of the tube wall that is disposed radially with respect to the first elongated element.

3. The catheter of claim 2, wherein the layer of the tube wall is integrally formed with a remaining part of the tube wall.

4. The catheter of claim 2, wherein the layer of the tube wall comprises a cover that is disposed over the first channel to cover the first elongated element, wherein the cover is secured to a remaining part of the tube wall.

5. The catheter of claim 2, wherein the layer of the tube wall comprises a tubular layer, and wherein the first part of the tube wall comprising the tubular layer is configured to deform to apply the first force against the first elongated element in response to the suction in the first channel.

6. The catheter of claim 2, wherein the layer is secured to a part of the tube wall by adhesive or friction; or
   wherein the layer is formed circumferentially around the part of the tube wall; or
   wherein the layer is laminated onto the part of the tube wall.

7. The catheter of claim 1, wherein the first elongated element has different cross-sectional dimensions at different respective locations along a length of the first elongated element.

8. The catheter of claim 1, wherein the first channel has different cross-sectional dimensions at different respective locations along a length of the first channel.

9. The catheter of claim 1, wherein the tube has a second channel in the tube wall, and wherein the catheter further comprises a second elongated element located in the second channel of the tube, the second elongated element slidably moveable in the second channel relative to the tube wall; and
   wherein a second part of the tube wall is configured to deform to apply a second force against the second elongated element.

10. The catheter of claim 9, wherein the suction port is configured to apply suction in both the first channel and the second channel.

11. The catheter of claim 9, wherein the first elongated element and the second elongated element have different respective lengths.

12. The catheter of claim 9, wherein the first elongated element and the second elongated element are on opposite sides of the tube.

13. The catheter of claim 1, further comprising:
    a first fluid channel in the tube wall; and
    a fluid delivery port configured to provide fluid in the first fluid channel.

14. The catheter of claim 13, wherein the first part of the tube wall is located between the first channel and the first fluid channel.

15. The catheter of claim 1, wherein the first portion of the first elongated element is immovable longitudinally with respect to the tube wall.

16. The catheter of claim 1, wherein the outer side that is configured to move radially more than the inner surface of the tube body when the suction is applied in the first channel comprises an exterior surface of the tube body.

17. The catheter of claim 16, wherein the first part of the tube wall extends from the exterior surface of the tube body, and is configured to move radially inward in response to the suction in the first channel.

18. The catheter of claim 1, wherein the first elongated element comprises other segments, and wherein none of the other segments is closer to the inner surface of the tube body than the segment of the first elongated element.

19. The catheter of claim 1, wherein the outer side of the tube body is a radially outer-most part of the tube body, wherein the center of the segment of the first elongated element is closer to the radially outer-most part of the tube body than to the inner surface of the tube body, thereby allowing the radially outer-most part of the tube body to move radially more than the inner surface of the tube body when the suction is applied in the first channel.

* * * * *